United States Patent [19]

Kurek et al.

[11] Patent Number: 5,319,683
[45] Date of Patent: Jun. 7, 1994

[54] CALIBRATION ARANGEMENT AND METHOD OF CALIBRATING AN INSPECTION INSTRUMENT

[75] Inventors: David Kurek, Greensburg; Daniel E. Klinvex, McKeesport; David S. Drinon, Oakmont, all of Pa.

[73] Assignee: Westinghouse Electric Corp., Pittsburgh, Pa.

[21] Appl. No.: 103,738

[22] Filed: Aug. 9, 1993

[51] Int. Cl.$^5$ .................................. G21C 17/00
[52] U.S. Cl. ............................... 376/245; 379/249
[58] Field of Search ....................... 376/245, 249, 252

[56] References Cited

U.S. PATENT DOCUMENTS

| | | | |
|---|---|---|---|
| 4,081,216 | 3/1978 | Cook | 356/256 |
| 4,097,837 | 6/1978 | Cyr | 340/5 C |
| 4,648,078 | 3/1987 | Darton et al. | 367/13 |
| 4,728,482 | 3/1988 | Boyle et al. | 379/249 |
| 4,838,070 | 6/1989 | Bradley | 73/1 DV |
| 4,903,523 | 2/1990 | Flynn | 73/1 DV |
| 4,966,746 | 10/1990 | Richardson et al. | 376/249 |
| 5,001,674 | 3/1991 | Kawasaki | 367/13 |
| 5,009,105 | 4/1991 | Richardson et al. | 376/249 |
| 5,163,027 | 11/1992 | Miller et al. | 367/13 |
| 5,165,280 | 11/1992 | Sternberg et al. | 73/622 |

*Primary Examiner*—Donald P. Walsh
*Assistant Examiner*—Frederick H. Voss
*Attorney, Agent, or Firm*—Walter S. Stevens

[57] ABSTRACT

Calibration arrangement and method for calibrating an inspection instrument, such as an ultrasonic inspection instrument of the kind typically used to inspect nuclear reactor pressure vessels. The calibration arrangement comprises a frame, the frame having a slot therethrough for receiving a sonic coupling medium therein. A plurality of channels extend through the frame and are in communication with the slot. A plurality of solid reflector rods matingly extend through respective ones of the channels and into the slot for reflecting sonic energy produced by a pulsed ultrasonic transducer mounted on the frame and spanning the slot. A pulser stimulates the transducer so that the transducer transmits pulsed sonic energy through the coupling medium which resides in the slot. The sonic energy is reflected by the rods that pass through the slot. The reflected sonic energy or echoes are received by the transducer, which generates transducer output signals that are received by a receiver. The receiver provides analog output signals that are converted by an analog-to-digital converter into digital output signals. A computer connected to the analog-to-digital converter evaluates the digital output signals. A display is connected to the computer for viewing the digital output signals. The digital output signals viewed on the display are therefore indicative of the orientations of the reflector rods in the frame for calibrating the transducer with respect to the orientations of the reflector rods in the frame.

24 Claims, 15 Drawing Sheets

CALIBRATION ARANGEMENT AND METHOD OF CALIBRATING AN INSPECTION INSTRUMENT

BACKGROUND

This invention generally relates to calibration apparatus and methods and more particularly relates to a calibration arrangement and method for calibrating an inspection instrument, such as an ultrasonic inspection instrument of the kind typically used to inspect nuclear reactor pressure vessels.

Although calibration devices and methods are known in the prior art, it has been observed that prior art devices and methods have certain operational problems associated with them which make these devices and methods unsuitable for calibrating inspection instruments of the kind typically used to inspect nuclear reactor pressure vessels. However, before these problems can be appreciated, some background is necessary as to the structure, operation and inspection of a typical nuclear reactor pressure vessel.

In this regard, a nuclear reactor pressure vessel is a device for producing heat by controlled fission of fissionable material contained in a reactor core disposed in the pressure vessel. Pressurized liquid moderator coolant (i.e., borated demineralized water) is caused to circulate through the pressure vessel, by means of inlet and outlet nozzles welded thereto, and through the reactor core for assisting in the fission process and for removing the heat produced by fission of the fissionable material contained in the reactor core. The heat provided by the reactor core is ultimately carried by the coolant to a turbine-generator set for providing revenue-producing electricity in a manner well known in the art of nuclear powered electricity generation.

However, there is a remote possibility that during its service life, the material comprising the pressure vessel may indicate anomalies. Such anomalies, if they were to occur, may be due, for example, to neutron radiation embrittlement and/or the corrosive effects of the borated moderator coolant. Therefore, ASME (American Society of Mechanical Engineers) Code, Section XI recommends that reactor pressure vessels be inspected for anomalies during the service life of the pressure vessels.

It is current practice to perform this inspection using ultrasonics. During the inspection, an ultrasonic inspection device is moved by remote means over a portion of the interior of the pressure vessel, such as over the pressure vessel interior wall, nozzles and weldments, to detect the size and severity of any anomalies therein. However, the operating response or output signals of the ultrasonic inspection device may vary on a daily basis or even hourly due to "drift", instrument component aging, or the like. Variation in the operating response of the ultrasonic inspection device may lead to inaccurate inspection results unless the inspection device is periodically re-calibrated by appropriate means.

To perform the initial calibration, a so-called "calibration block" is used to calibrate the ultrasonic inspection device. The calibration block of current practice comprises a five to nine inch thick and relatively heavy steel block having at least one hole therein to simulate an anomaly of the type that may be encountered in the pressure vessel (e.g., the pressure vessel wall, nozzles and weldments). In this regard, an ultrasonic transducer is brought into contact with and moved on the surface of the calibration block to direct ultrasonic energy in the direction of the hole, which is located at a predetermined distance or depth within the block. The steel material of the block serves as the sound transmission or sonic coupling medium that sonically couples the hole to the ultrasonic transducer, so that a response is obtained from the hole. More specifically, the ultrasonic transmission, which may be either a shear wave or longitudinal wave sound transmission, is introduced into the block at refracted angles of between 0 degrees to 70 degrees. A return echo with a characteristic amplitude is produced when the sonic energy encounters the hole. The return echo is detected by the ultrasonic transducer, which generates a signal indicative of the depth and orientation of the hole in the steel block. In this manner, the calibration block calibrates the ultrasonic device so that it is capable of suitably alerting the test operator when similarly shaped anomalies are detected in the pressure vessel. Once the initial calibration of the system has been established, the initial calibration is usually verified or validated by re-calibration at approximately 12-hour intervals during the pressure vessel examination because, as previously mentioned, the response of the device may vary over time. In the prior art, this validation or re-calibration effort is customarily performed on the previously mentioned steel calibration block in the same manner as the original calibration.

However, it is current practice to place the calibration block externally to the pressure vessel. This necessitates that, during the process of pressure vessel examination, the ultrasonic transducer be remotely retrieved from the pressure vessel and placed on the calibration block. Each retrieval of the ultrasonic transducer requires that nonessential maintenance personnel in the vicinity of the pressure vessel leave the area as the transducer is removed from the pressure vessel in order to avoid radiation exposure to the maintenance personnel. If they were to remain in the vicinity of the pressure vessel as the transducer is retrieved from the vessel, such personnel would be exposed to radiation because the transducer is radioactively contaminated during its tenure in the pressure vessel. These personnel re-enter the vicinity of the pressure vessel after the transducer is reintroduced into the vessel following re-calibration because once the transducer is inside the pressure vessel, the pressure vessel and liquid moderator therein shield the personnel against radiation emanating from the radioactively contaminated transducer. However, such time consuming exit and re-entry of maintenance personnel results in nonproductive or lost time which in turn increases maintenance costs because such maintenance personnel are not performing maintenance activities while away from the pressure vessel. Therefore, a problem in the art is to perform the required re-calibration or validation in a manner not necessitating the exit and re-entry of such maintenance personnel, so that maintenance costs are reduced.

Also, the time dedicated to retrieving the transducer from and reintroducing the transducer into the pressure vessel may delay returning the reactor to service, if the inspection is performed on the critical path for completion of all pressure vessel maintenance activities. Any such delay in returning the reactor to service may result in lost revenue of approximately $1,000,000 per day for the utility owner. Therefore, a problem in the art is to perform the validation in a more time-efficient and hence cost-effective manner that obviates the need to retrieve and then reintroduce the transducer into the vessel, so that there is no delay in returning the pressure vessel to service.

Moreover, certain essential maintenance personnel required to perform the original calibration and subsequent validation must remain in the vicinity of the pressure vessel. Such essential maintenance personnel may be exposed to low doses of radiation during the re-calibration or validation process. Although such radiation doses are within acceptable limits, it is nonetheless desirable to lower the level of such radiation doses. Therefore, another problem in the art is to perform the re-calibration or validation in a manner that lowers radiation doses to such essential maintenance personnel.

Therefore, what is needed is a calibration arrangement and method for calibrating an inspection instrument, such as an ultrasonic inspection instrument of the kind typically used to inspect nuclear reactor pressure vessels.

SUMMARY

Disclosed herein are a calibration arrangement and method for calibrating an inspection instrument, such as an ultrasonic inspection instrument of the kind typically used to inspect nuclear reactor pressure vessels. The calibration arrangement comprises a frame formed of a homogeneous material, the frame having a slot therethrough for receiving a sonic coupling medium therein. A plurality of channels extend through the frame and are in communication with the slot. A plurality of solid reflector rods matingly extend through respective ones of the channels and through the slot for reflecting sonic energy produced by a pulsed ultrasonic transducer mounted on the frame and over the slot. A pulser stimulates the transducer so that the transducer transmits pulsed sonic energy through the coupling medium which resides in the slot. The sonic energy is reflected by the rods that pass through the slot. The reflected sonic energy or echoes are received by the transducer, which generates transducer output signals that are received by a receiver. The receiver provides analog output signals that are converted by an analog-to-digital converter which converts the analog output signals into digital output signals. A computer connected to the analog-to-digital converter evaluates the digital output signals. A display is connected to the computer for viewing the digital output signals in graphical form. It will be appreciated that the transducer output signals are therefore related to and indicative of the locations and orientations of the reflector rods for calibrating the transducer with respect to the locations and orientations of the reflector rods.

In its broad form, the invention is a calibration arrangement for calibrating an inspection instrument capable of transmitting and receiving sonic energy, the instrument capable of generating a signal in response to the sonic energy received thereby, comprising a frame having a slot for receiving a coupling medium therein and having a channel in communication with the slot, the channel having a predetermined orientation with respect to the instrument; and a reflector extending through the channel and into the slot for reflecting the sonic energy, said reflector having the predetermined orientation of the channel, whereby an echo associated with the predetermined orientation of said reflector is produced as said reflector reflects the sonic energy, and whereby the echo travels through the coupling medium and is received by the instrument to generate the signal, the signal being indicative of the predetermined orientation of said reflector for calibrating the instrument with respect to the predetermined orientation of said reflector.

In its broad form, the invention is also a method of calibrating an inspection instrument capable of transmitting and receiving sonic energy, the instrument capable of generating a signal in response to the sonic energy received thereby, comprising the steps of providing a frame having a slot for receiving a coupling medium therein and having a channel in communication with the slot, the channel having a predetermined orientation with respect to the instrument, the channel having a reflector extending therethrough so that the reflector has the predetermined orientation of the channel and so that the reflector extends into its associated slot for reflecting the sonic energy therefrom; and operating the instrument to transmit the sonic energy through the coupling medium so that the sonic energy is intercepted by the reflector and reflected through the coupling medium to produce an echo capable of being received by the instrument, the echo being indicative of the predetermined orientation of the reflector for calibrating the instrument with respect to the predetermined orientation of the reflector.

An object of the present invention is to provide a calibration arrangement and method for calibrating an inspection instrument, such as an ultrasonic inspection instrument of the kind typically used to inspect nuclear reactor pressure vessels.

Another object of the present invention is to provide a calibration arrangement and method for calibrating an inspection instrument, which calibration arrangement and method does not require that the inspection instrument be repeatedly retrieved from and re-introduced into the pressure vessel in order to perform the calibration.

Yet another object of the present invention is to provide a calibration arrangement and method that reduces radiation exposure to maintenance personnel performing the calibration.

A feature of the present invention is the provision of a frame for slidably mounting the inspection instrument thereon, the frame having a slot for receiving a coupling medium therein and a channel in communication with the slot, the channel having a predetermined location and orientation with respect to the inspection instrument mounted on the frame.

Another feature of the present invention is the provision of a solid reflector rod matingly disposed in the channel such that the rod has the predetermined orientation of the channel, the rod capable of reflecting sonic energy transmitted by the inspection instrument, the reflected sonic energy being indicative of the location and orientation of the rod.

An advantage of the present invention is that it reduces maintenance costs because nonessential maintenance personnel need not leave the area of the pressure vessel to avoid radiation exposure during calibration of the inspection instrument due to the fact that the calibration is performed in a shielding medium (i.e., water).

Another advantage of the present invention is that radiation dose levels to essential maintenance personnel performing the calibration are reduced because such personnel are not repeatedly exposed to the radioactively contaminated inspection instrument during the calibration process.

Yet another advantage of the present invention is that revenue is not lost due to delays in returning the pressure vessel to service because the inspection instrument need not be repeatedly retrieved from and reintroduced into the pressure vessel in order to perform the required number of calibrations.

These and other objects, features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings wherein:

DESCRIPTION OF THE PREFERRED EMBODIMENTS

Disclosed hereinbelow are a calibration arrangement and method for calibrating an inspection instrument, such as an ultrasonic inspection instrument of the kind typically used to inspect nuclear reactor pressure vessels.

However, before describing the subject matter of the present invention, it is instructive first to briefly describe the structure, operation and inspection of a typical nuclear reactor pressure vessel.

Figure 1:
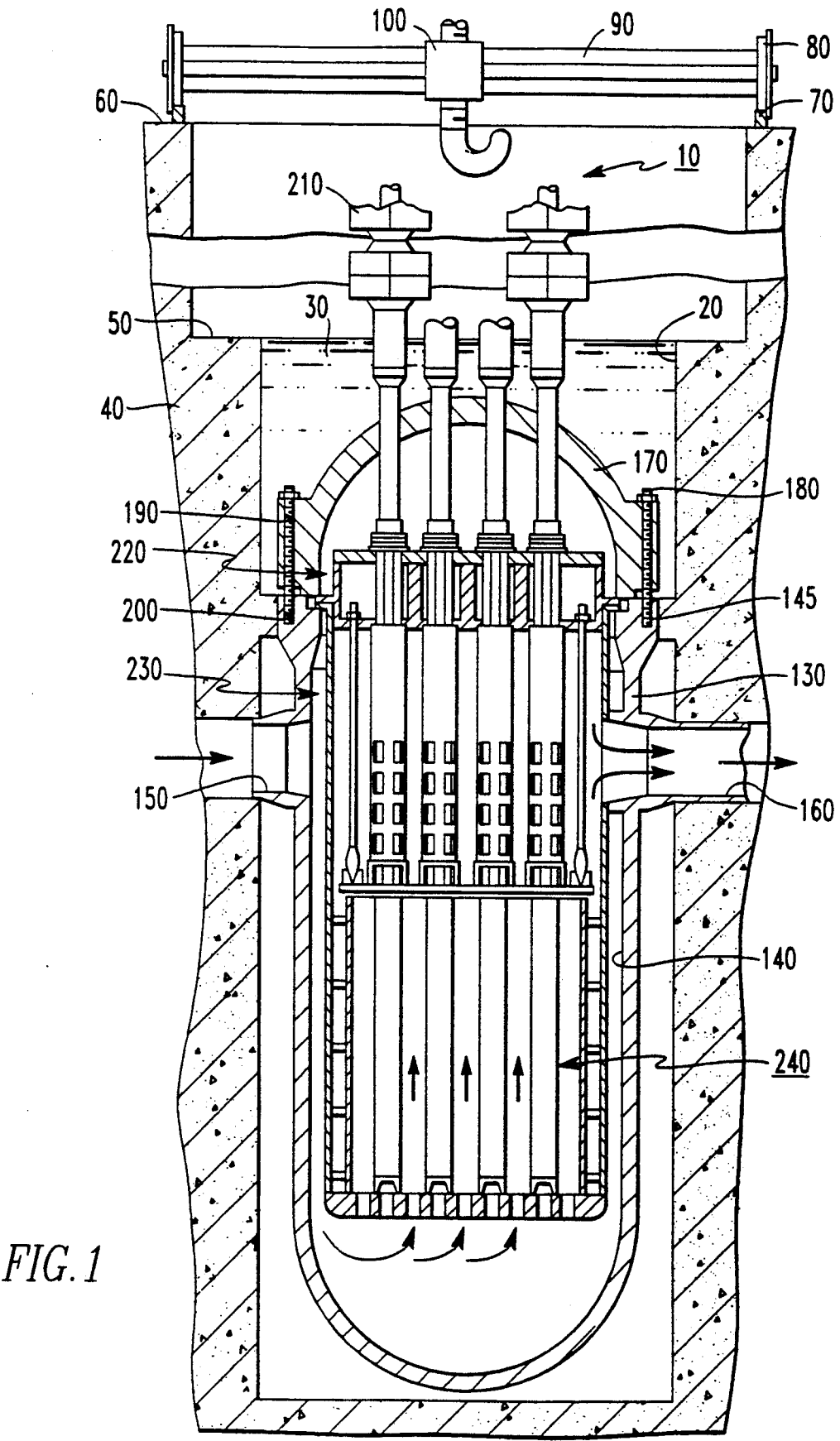
FIG. 1 shows in partial vertical section, a typical nuclear reactor pressure vessel with parts removed for clarity, the pressure vessel disposed in a reactor cavity and including a closure head, the cavity having a movable bridge disposed above the closure head and an adjustable manipulator assembly connected to the bridge, the manipulator assembly having an inspection instrument connected thereto.
Figure 2:
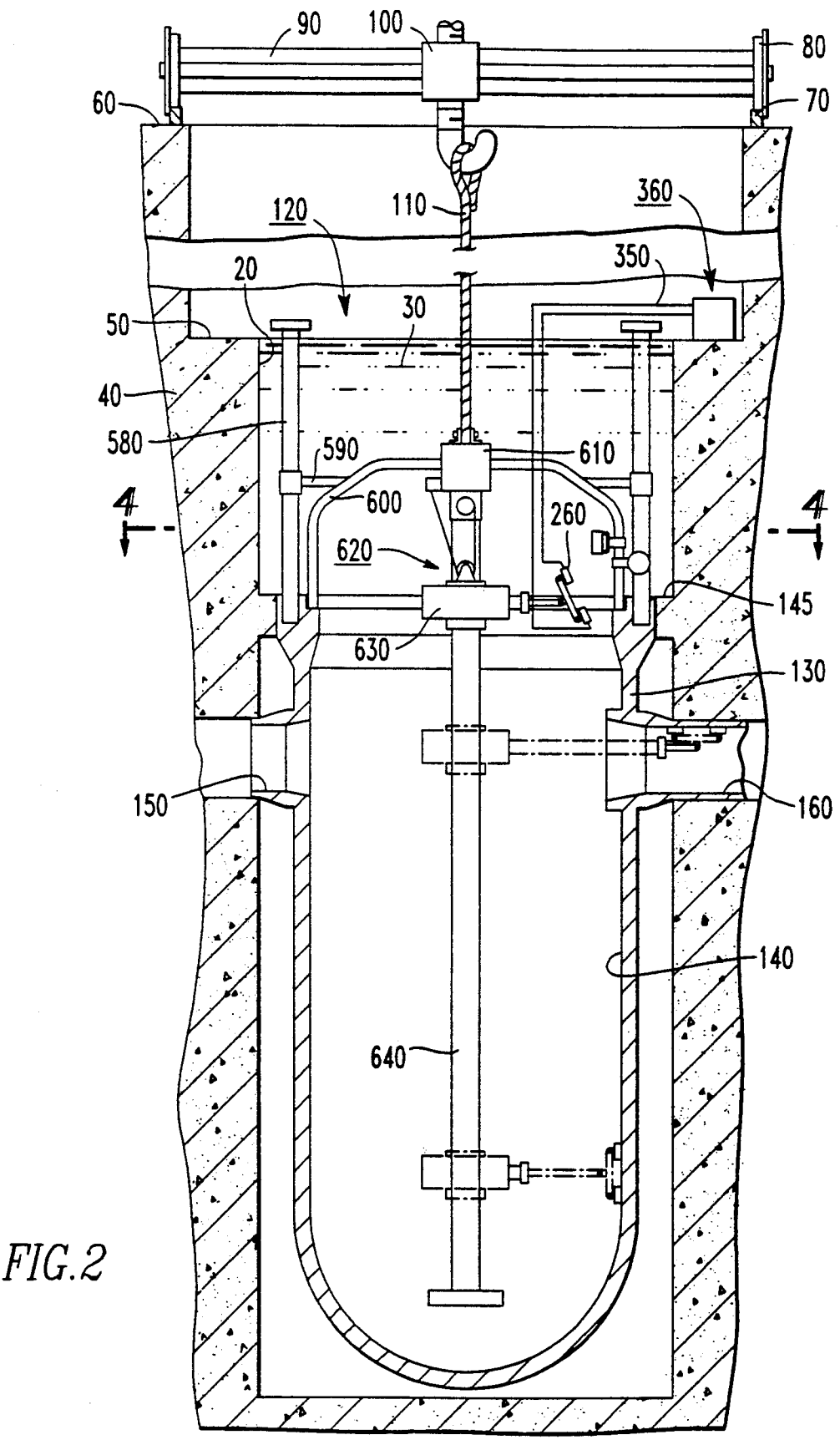
FIG. 2 shows in vertical section, the pressure vessel having the closure head removed therefrom and the manipulator assembly, calibration arrangements, and inspection instrument lowered into the pressure vessel, the inspection instrument having an evaluation system connected thereto for evaluating output signals generated by the inspection instrument.

Therefore, referring to FIGS. 1 and 2, there is shown a typical nuclear reactor pressure vessel, generally referred to as 10, for producing heat by controlled fission of fissionable material (not shown). Reactor pressure vessel 10 is disposed in a reactor cavity 20 having a liquid medium 30 (i.e., borated demineralized water) for moderating the fission process and for shielding the environment surrounding pressure vessel 10 from nuclear radiation. Medium 30 also may serve as a sonic coupling medium, as described in more detail hereinbelow. Reactor cavity 20 is defined by a containment structure 40 which may have a landing 50 thereon. Containment structure 40 also has a top surface 60 to which is attached a rail 70 disposed near cavity 20. Slidably engaging rail 70 are a plurality of motorized wheels 80 rotatably affixed to either end of an elongate bridge 90 for moving bridge 90 as wheels 80 roll on rail 70. Slidably engaging bridge 90 is a motorized conveyor 100 adapted to slidably translate along elongate bridge 90. Engaging conveyor 100 is a cable 110 from which is suspended a manipulator assembly 120 for reasons disclosed hereinbelow. Conveyor 100 is capable of raising manipulator assembly 120 upwardly from and lowering manipulator assembly 120 downwardly into cavity 20 for reasons disclosed hereinbelow.

Still referring to FIGS. 1 and 2, pressure vessel 10 includes a pressure vessel shell 130 open at its top end and having an inner surface 140 and a plurality of inlet nozzles 150 and outlet nozzles 160 attached, such as by welding, to the upper portion thereof (only one of each nozzle is shown). The top end of pressure vessel shell 130 has a top surface 145 thereon defining an annular ledge 147. A hemispherical pressure vessel closure head 170 is mounted atop vessel shell 130 and is sealingly attached to the open top end of vessel shell 130, such as by a plurality of hold-down bolts 180, so that closure head 170 sealingly caps vessel shell 130. In this regard, each hold-down bolt 180 extends through a bore 190 formed in closure head 170 and has an end thereof threadably received in a bore 200 formed in top surface 145 of pressure vessel shell 130. Sealingly extending through closure head 170 are a plurality of control rod drive mechanisms 210 for controlling the fission process in pressure vessel 10 in a manner well known in the art. Control rod drive mechanisms 210 are connected to an upper internals structure, generally referred to as 220, which is disposed in pressure vessel 10 for supporting control rod drive mechanisms 210. Upper internals structure 220 is mounted atop a lower internals structure, generally referred to as 230. Moreover, disposed in pressure vessel 10 is a nuclear reactor core, generally referred to as 240, which is supported by lower internals structure 230. Reactor core 240 itself contains the fissionable material for generating heat.

As nuclear reactor pressure vessel 10 operates, coolant (not shown), which is the previously mentioned borated demineralized water, enters shell 130 and circulates therethrough generally in the direction of the arrows shown in FIG. 1. As the coolant circulates through shell 130, it also circulates through reactor core 240 for assisting in the fission process and for removing the heat produced by fission of the fissionable material contained in reactor core 240. Control rod drive mechanisms 210 control the fission process in reactor core 240 as the fission heat generated by the fission process is ultimately transferred to a turbine-generator set (not shown) for providing revenue-producing electricity in a manner well known in the art.

However, there is a remote possibility that during its service life, the material (e.g., stainless steel) comprising pressure vessel 10 may indicate anomalies. These anomalies may, for example, be voids, porosity, cracks and delaminations. Such anomalies, if they occur, may be due, for example, to neutron radiation embrittlement and/or the corrosive effects of the borated moderator coolant. Therefore, pressure vessel 10 is inspected for anomalies using a suitable inspection instrument that has been previously calibrated to a known standard. However, this inspection instrument is preferably periodically recalibrated to the known standard to ensure that it continues to accurately inspect pressure vessel 10 for anomalies during the relatively long inspection process.

Therefore, referring to FIGS. 2, 3, 4, 5, 6 and 7, there is shown a first embodiment calibration arrangement, generally referred to as 250, for calibrating an inspection instrument, such as a piezoelectric ultrasonic transducer 260 of the kind typically used to inspect nuclear reactor pressure vessels. It will be appreciated that first embodiment calibration arrangement 250 is particularly useful for calibrating transducer 260 in a manner such that transducer 260 will accurately inspect surface 140 for anomalies. Calibration arrangement 250 comprises a first embodiment frame 270 having a generally rectangularly-shaped transverse cross section and having a planer top surface 280 for slidably mounting ultrasonic transducer 260 thereon. In addition, frame 270 has a plurality of parallel spaced-apart slots 290 therethrough for receiving sonic coupling medium 30, which sonic coupling medium 30 may be the reactor coolant. Frame 270 also has a plurality of spaced-apart round elongate channels 300 extending therethrough in communication with associated ones of the slots 290 for reasons disclosed presently. Each of the channels 300 has a predetermined depth and orientation or angle with respect to surface 280 and thus has a predetermined depth and orientation or angle with respect to transducer 260 which is slidably mountable on surface 280. Preferably, each channel 220 is disposed parallel with respect to surface 280 and is spaced a predetermined distance from top surface 280. Moreover, frame 270 may have a plurality of internally threaded bores 310 for reasons disclosed in more detail hereinbelow. Frame 270 may be formed of a polymer material such as "LUCITE", or the like, for reducing the weight of frame 270. In this regard, "LUCITE" comprises polymethylmethacrylate and is available from E. I. DuPont De Nemours and Company located in Wilmington, Del.

Still referring to FIGS. 2, 3, 4, 5, 6 and 7, extending matingly through respective ones of channels 300 and into associated ones of slots 290 are a plurality of reflectors, which may be elongate generally cylindrical solid and rigid metal reflector rods 320, for intercepting and reflecting the sonic energy transmitted by transducer 260. In this regard, rods 320 may be stainless steel or the like for intercepting and reflecting the sonic energy. Hence, it will be appreciated from the description hereinabove that each of the rods 320 assumes the predetermined angle of its respective channel 220 as it extends through its respective channel 220.

Figure 6:
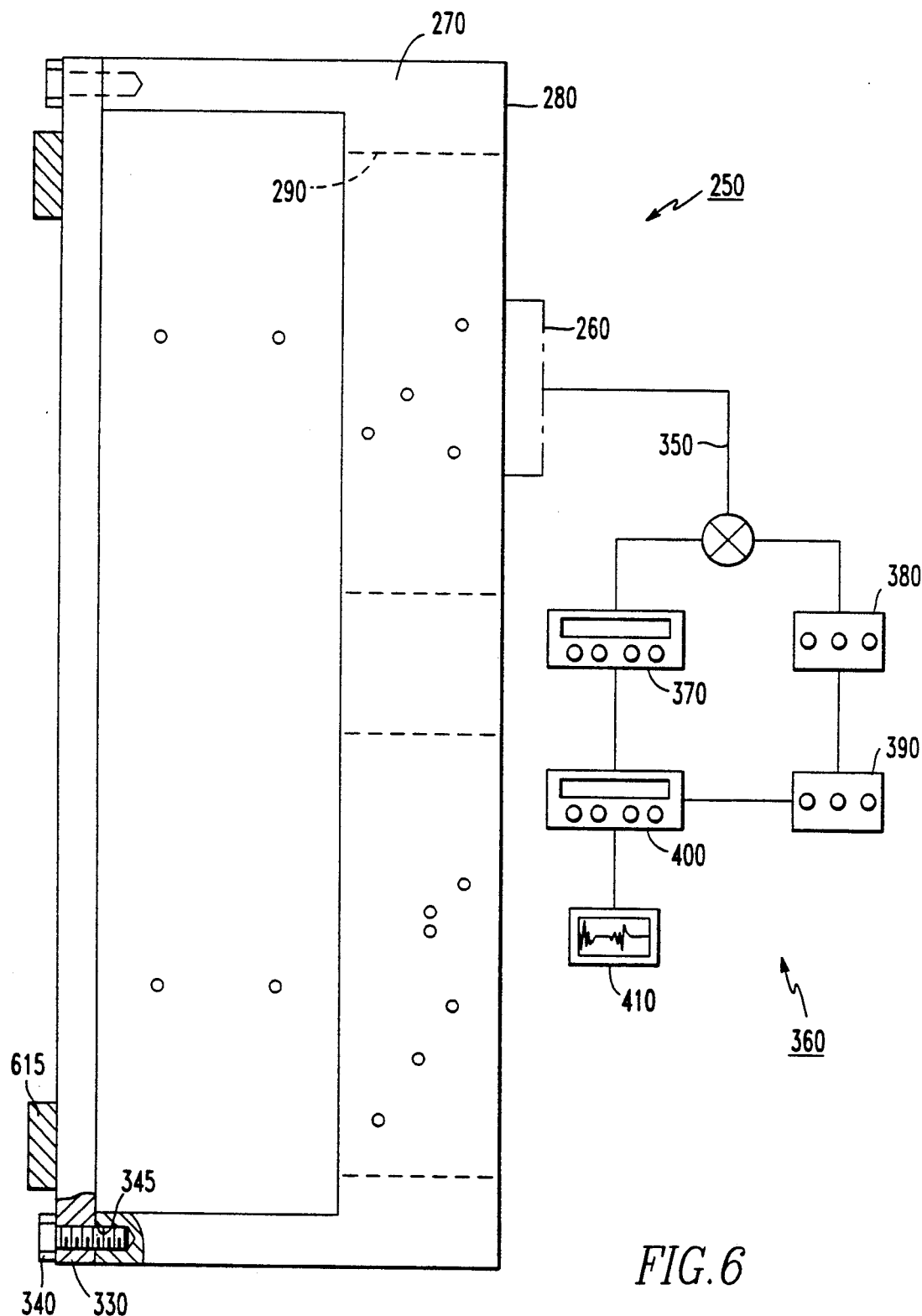
FIG. 6 is a lateral view in elevation of the first embodiment calibration arrangement taken along section line 6—6 of FIG. 5.
Figure 7:
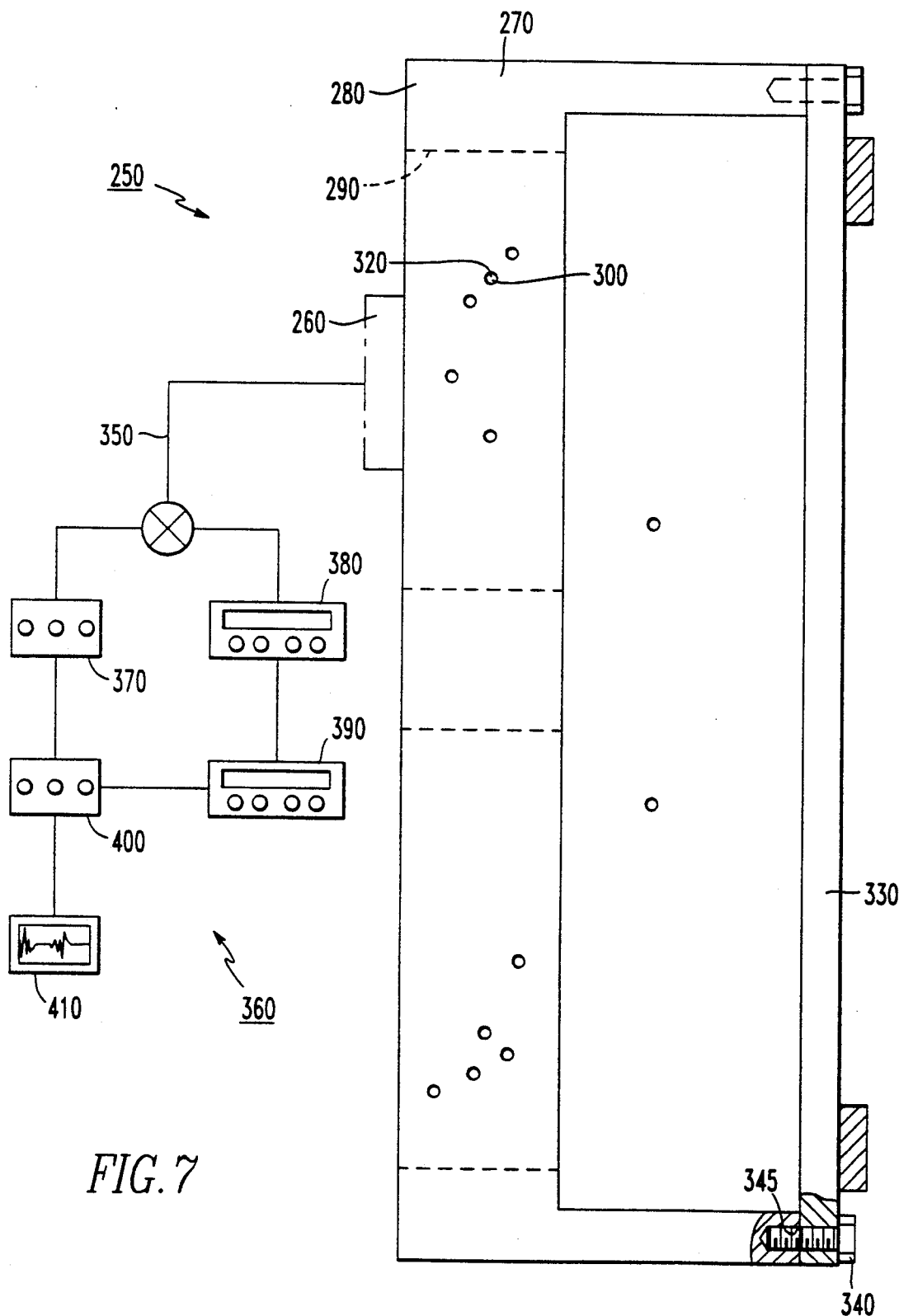
FIG. 7 is a lateral view in elevation of the first embodiment calibration arrangement taken along section line 7—7 of FIG. 5.
Figure 8:
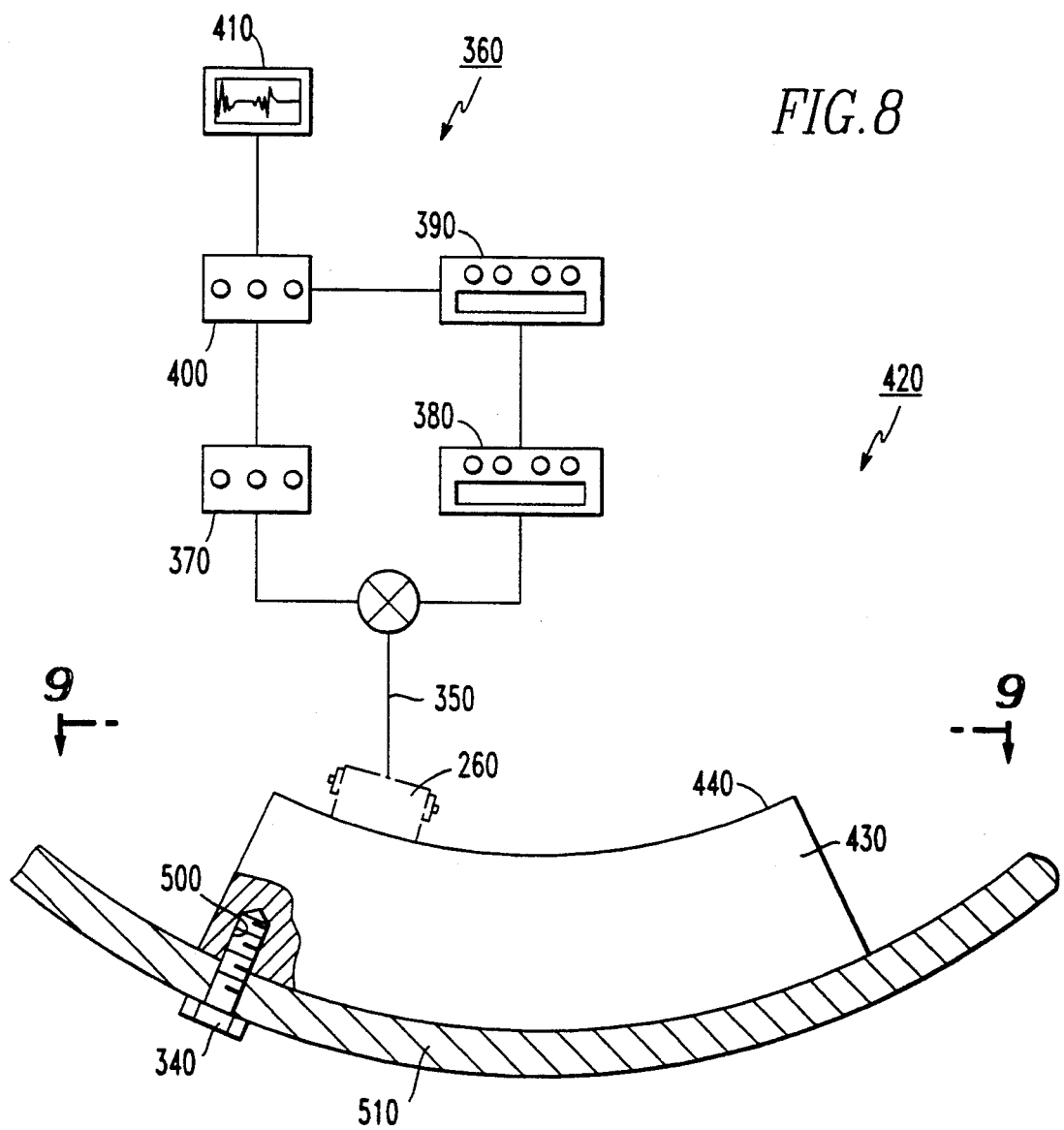
FIG. 8 is a view in elevation of a second embodiment calibration arrangement.
Figure 9:
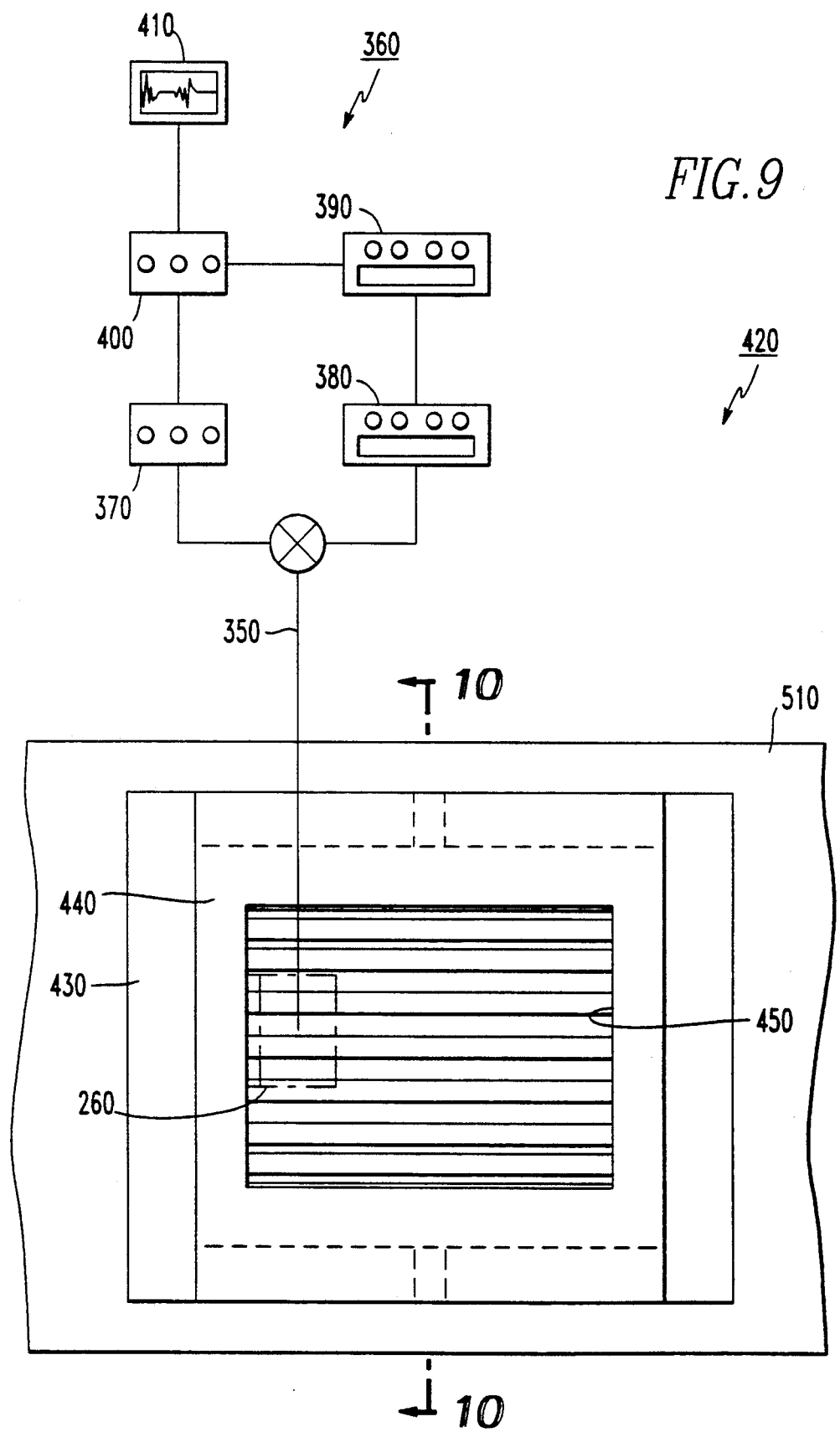
FIG. 9 is a view taken along section line 9—9 of FIG. 8.
Figure 10:
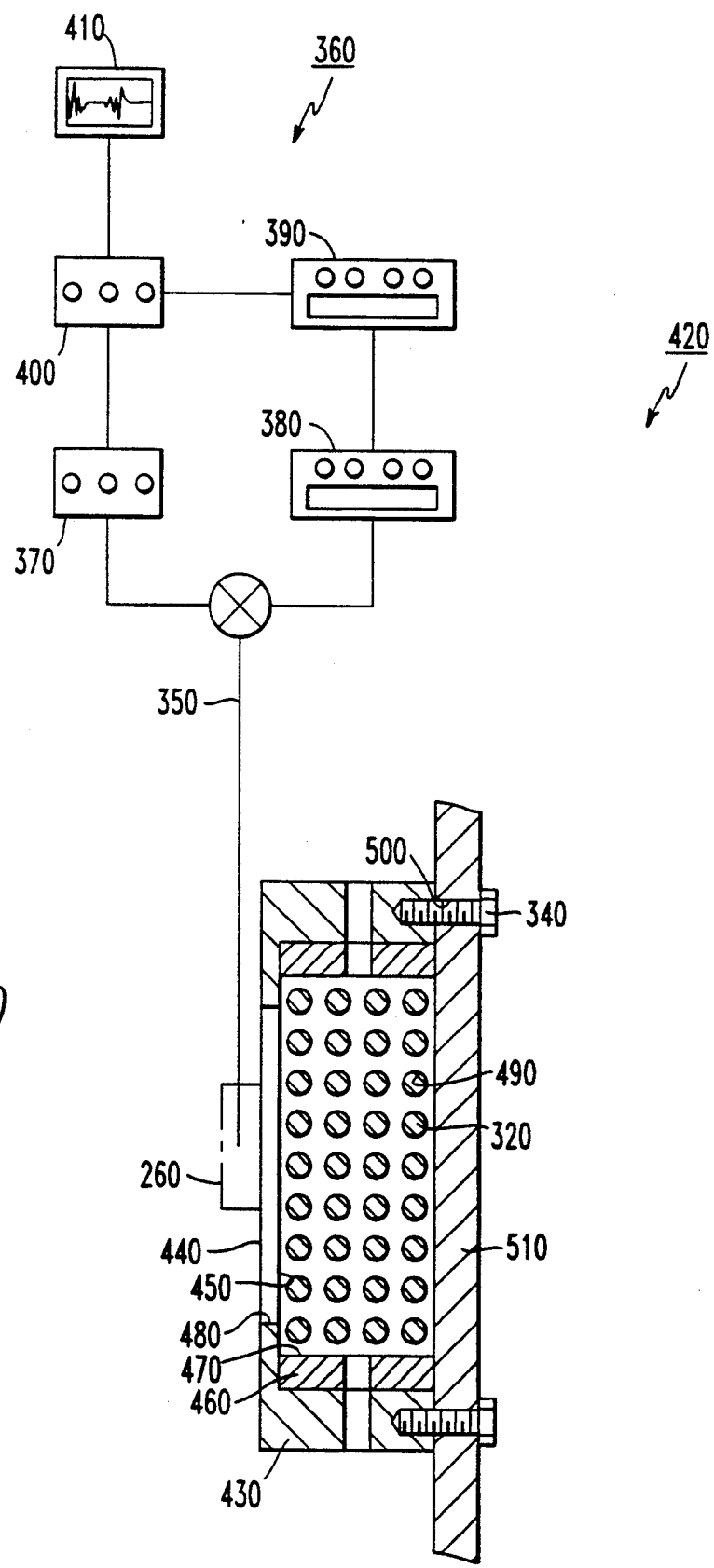
FIG. 10 is a view taken along section line 10—10 of FIG. 9.
Figure 11:
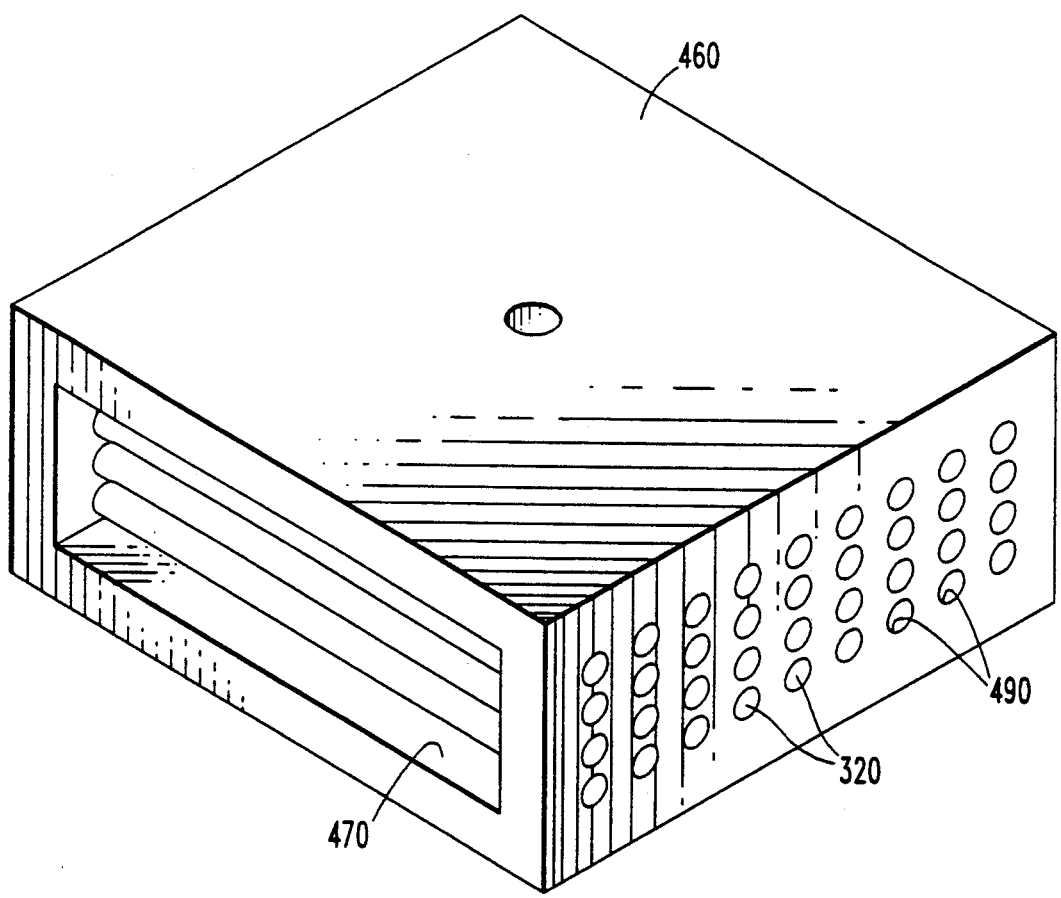
FIG. 11 is a view in elevation of an insert insertable within a recess of the second embodiment calibration arrangement.
Figure 12:
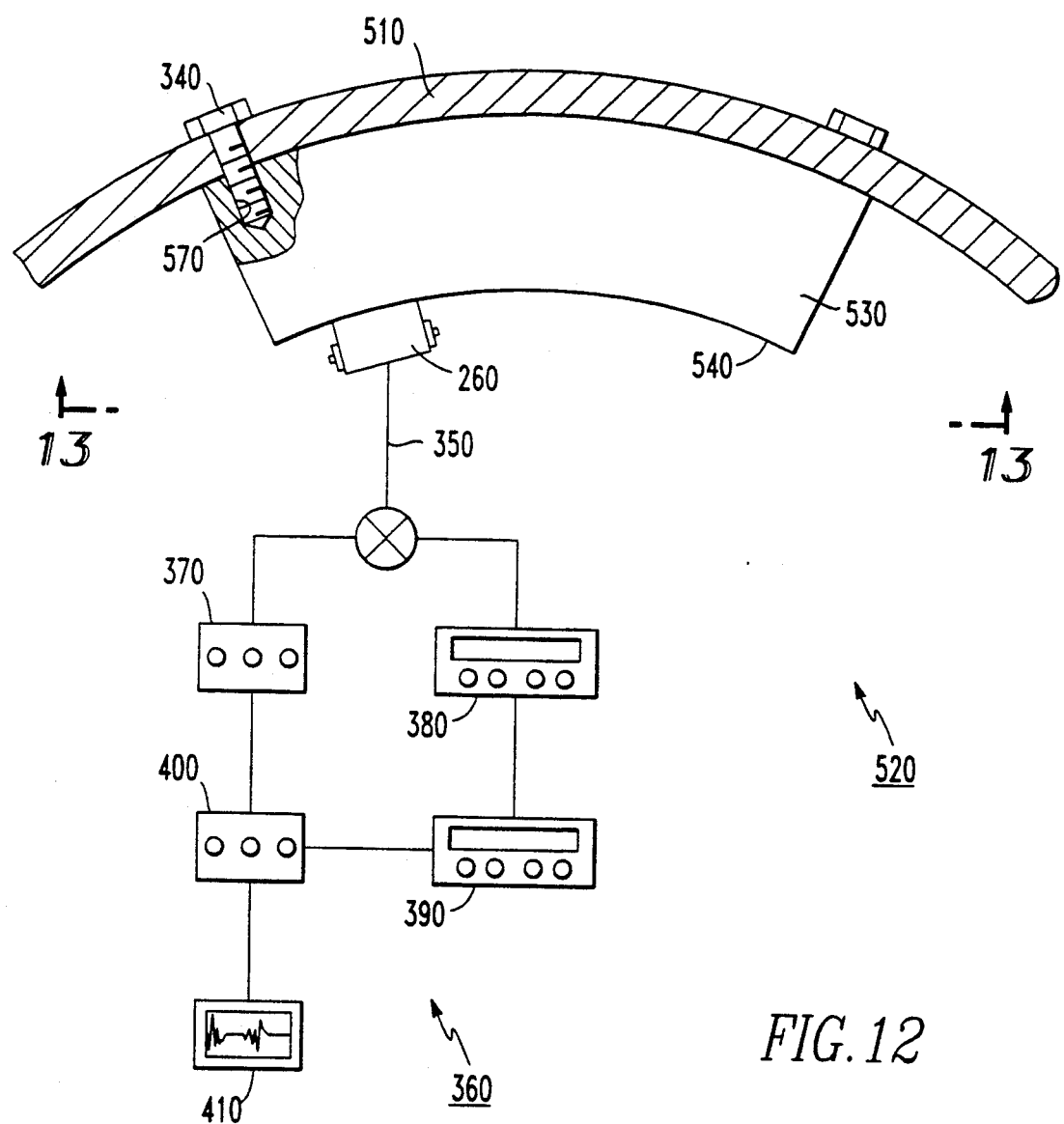
FIG. 12 is a side view in elevation of a third embodiment calibration arrangement.
Figure 13:
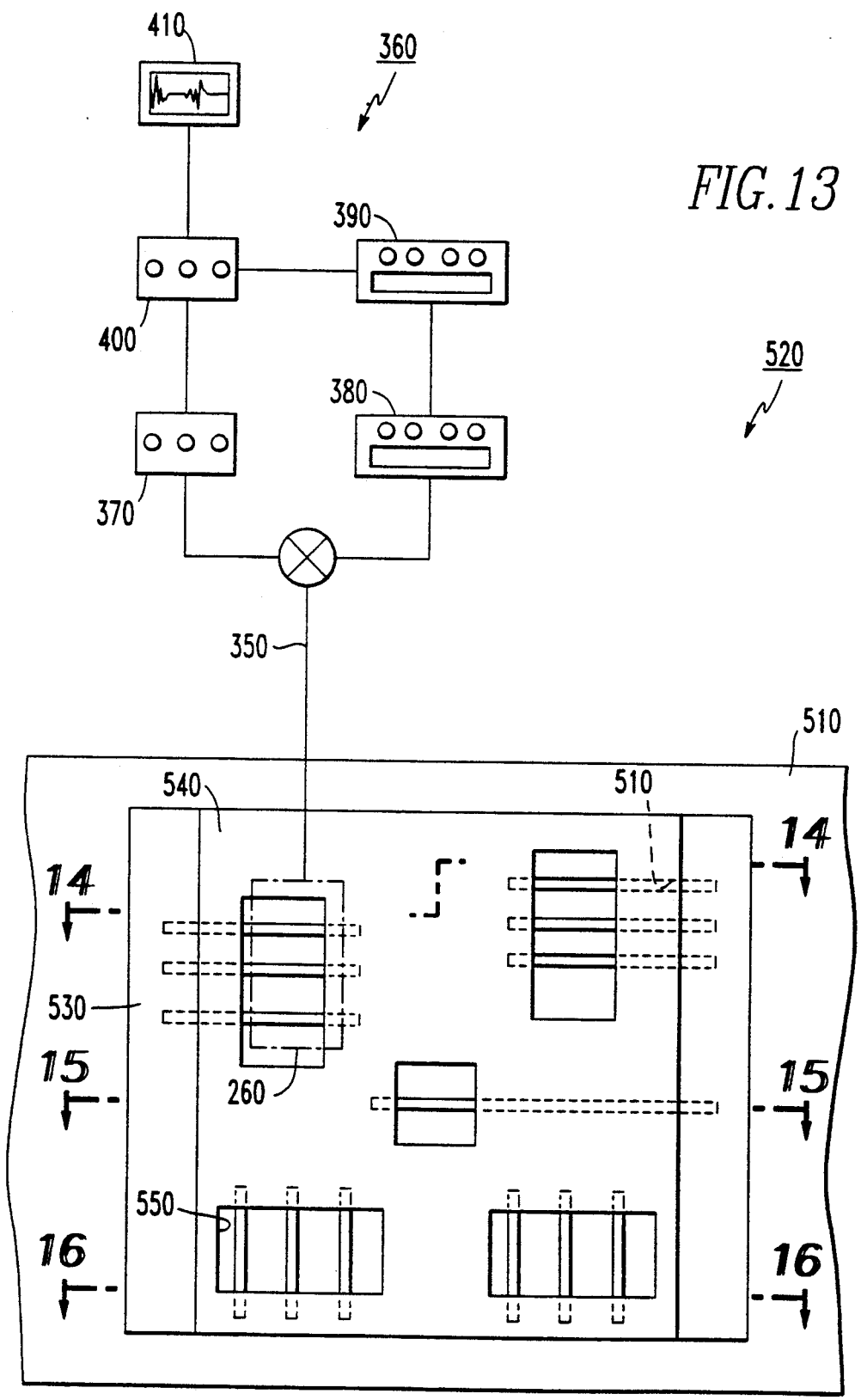
FIG. 13 is a plan view in elevation of the third embodiment calibration arrangement.
Figure 14:
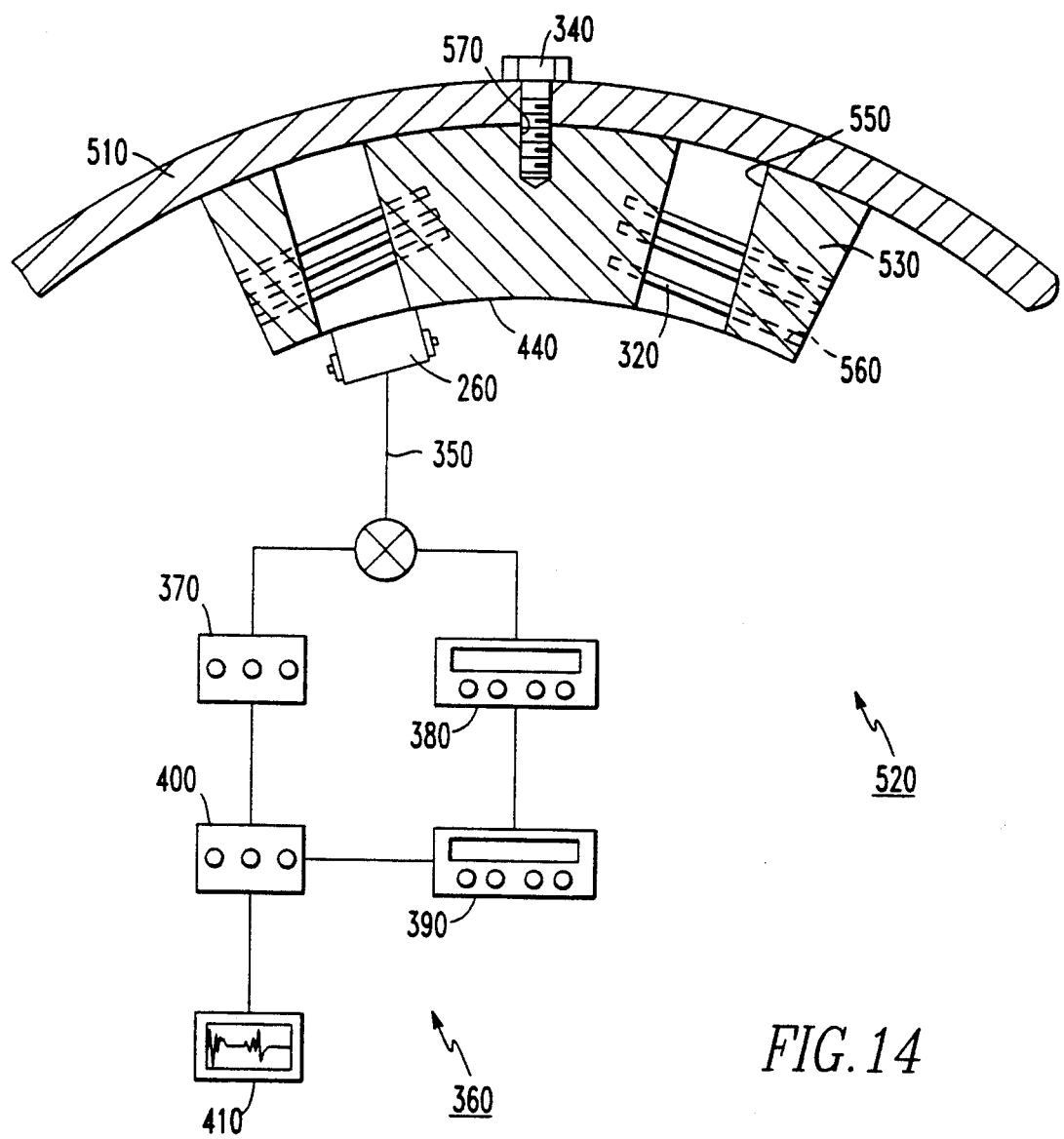
FIG. 14 is a view taken along section line 14—14 of FIG. 13.
Figure 15:
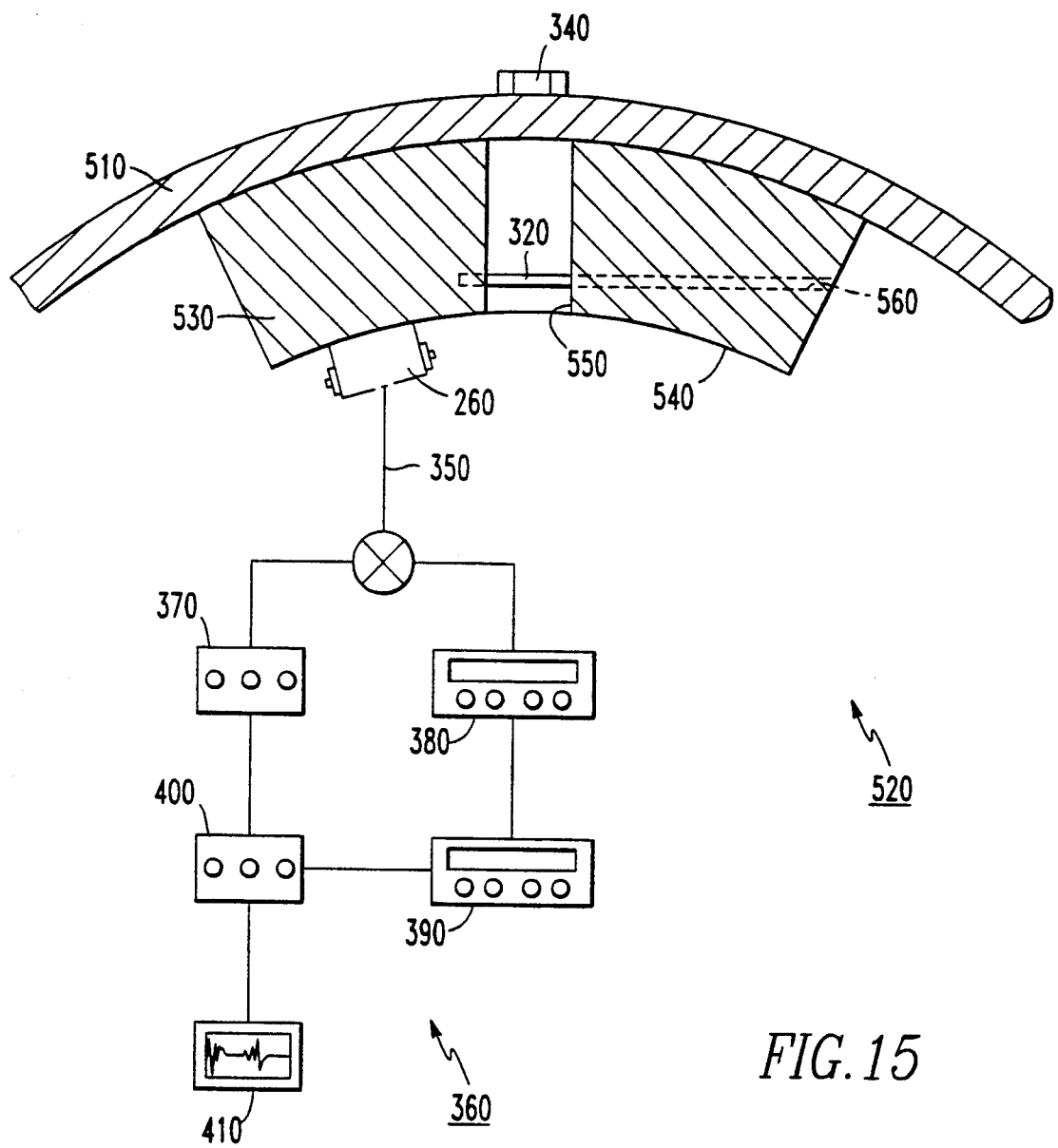
FIG. 15 is a view taken along section line 15—15 of FIG. 13.
Figure 16:
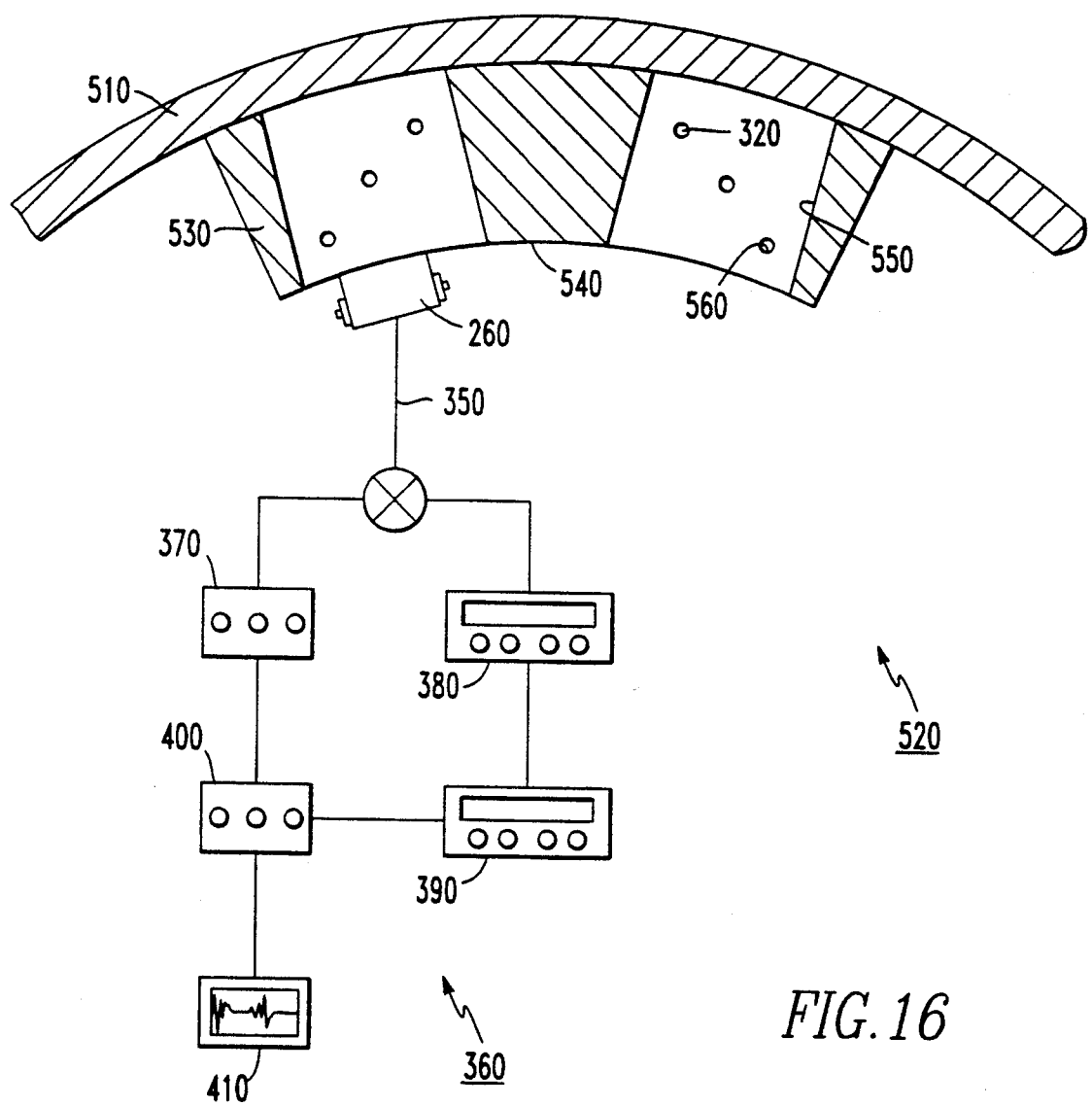
FIG. 16 is a view taken along section line 16—16 of FIG. 13.

As best seen in FIG. 6, frame 270 rests on a seat 330. Frame 270 is attached to seat 330, such as by externally threaded screw bolts 340 that extend through seat 330 and that are threadably received in respective ones of internally threaded bores 345, for threadably securing frame 270 to seat 330.

Returning to FIGS. 2, 3, 4, 5, 6 and 7, electrically connected to transducer 260, such as by an electrical conducting wire 350, is an evaluation system, generally referred to as 360, for evaluating the output signals generated by transducer 260. Evaluation system 360, which may be disposed on land 50 so that it is sufficiently near pressure vessel 10, comprises a pulser device 370 electrically connected to transducer 260 for electrically stimulating transducer 260 in such a manner that transducer 260 periodically transmits pulsed sonic energy spaced apart in time, the sonic energy being directed through coupling medium 30 to be intercepted by rods 320 which reflect the sonic energy with a characteristic amplitude. A receiver 380 is electrically connected to transducer 260 for receiving the transducer output signals generated by transducer 260 as transducer 260 receives the sonic energy reflected by rods 320 (i.e., echoes reflected by rods 320). Receiver 380 in turn provides a plurality of analog output signals as receiver 380 receives the transducer output signals. An analog-to-digital converter 390 is electrically connected to receiver 380 for converting the analog output signals into a plurality of digital output signals. A computer 400 is electrically connected to analog-to-digital converter 390 for evaluating the digital output signals and is also electrically connected to pulser device 370 for operating pulser device 370 to periodically stimulate transducer 260. In addition, electrically connected to computer 400 is a graphic display 410 for viewing the digital output signals being evaluated by computer 400.

Turning now to FIGS. 8, 9, 10 and 11, there is shown a second embodiment of the invention, which is a second embodiment calibration arrangement, generally referred to as 420, for calibrating transducer 260. It will be appreciated that calibration arrangement 420 is particularly useful for calibrating transducer 260 such that transducer 260 accurately inspects nozzles 150/160 for anomalies. Calibration arrangement 420 comprises a frame 430 having a generally wedge-shaped or arcuate-shaped transverse cross section having a curved or convex top surface 440 for slidably mounting ultrasonic transducer 260 thereon. Curved surface 540 preferably defines an approximate 24 degree arc. Therefore, when transducer 260 is slidably mounted on top surface 440, it is capable of being slidably moved through an approximate 24 degree arc on convex top surface 440. Frame 430 has a recess 450 formed therein for matingly receiving an insert 460. Insert 460 has a generally rectangularly-shaped traverse cross section and also has a hole 470 longitudinally therethrough for receiving the sonic coupling medium 30 therein. In addition, frame 530 has a slot 480 therethrough aligned with hole 470 and in fluid communication therewith for conducting the sonic coupling medium 30 (i.e., the water filling cavity 20 and vessel shell 130) through slot 480 and into hole 470.

Moreover, insert 460 has a plurality of spaced-apart round elongate channels 490 extending transversely therethrough and in communication with the hole 470. Each of the channels 490 has a predetermined orientation or angle with respect to top surface 440 and thus with respect to transducer 260, which transducer 260 is mountable on top surface 440. Preferably, each channel 410 is disposed generally parallel with respect to top surface 440. In addition, each channel 490 is spaced a predetermined depth or distance from top surface 440. Moreover, frame 430 has a plurality of internally threaded bores 500 for threadably receiving externally threaded screw bolts 340 for reasons disclosed presently. In this regard, frame 530 is attached to a circular or hoop-like seat 510 by screw bolts 340, which screw bolts 340 extend through seat 510 and are threadably received in respective ones of bores 500, for securing frame 430 to seat 510. Extending matingly through respective ones of channels 490 and into hole 470 are reflector rods 320 for reflecting the sonic energy. Hence, it will be understood from the description hereinabove that each of the rods 320 has the predetermined depth and orientation or angle of its respective channel 490 as it extends through its respective channel 490. It will be further understood from the description hereinabove, that frame 430 obtains a modular construction in the sense that recess 450 is capable of receiving a different insert 460 having differing numbers and orientations of rods 320, if desired. That is, the insert 460 shown in the several figures may be quickly retrieved from recess 450 and a different insert (not shown) having a different number of rods 320 with associated orientations may be substituted for insert 460, if desired. Frame 430 may be formed of a polymer material such as "LUCITE", or the like, to reduce the weight of frame 430.

Referring now to FIGS. 12, 13, 14, 15 and 16, there is shown a third embodiment of the invention, which is a third embodiment calibration arrangement, generally referred to as 520, for calibrating transducer 260. It will be appreciated that third embodiment calibration arrangement 520 is particularly useful for calibrating transducer 260, such that transducer 260 accurately inspects nozzle 150 (or nozzle 130) for anomalies. Calibration arrangement 520 comprises a frame 530 having a generally wedge-shaped or arcuate-shaped transverse cross section having a curved or convex top surface 540 for slidably mounting ultrasonic transducer 260 thereon, such that transducer 260 is movable linearly along top surface 540 (i.e., transversely with respect to the curvature top surface 540). In addition, frame 530 has a plurality of spaced-apart slots 550 therethrough for receiving the sonic coupling medium 30 therein. Frame 530 also has a plurality of spaced-apart round elongate channels 560 extending transversely therethrough in communication with associated ones of the slots 550. Each channel 560 has a predetermined orientation or angle with respect to top surface 540 and thus has a predetermined orientation or angle with respect to transducer 260, which is mountable on top surface 540. Preferably, each channel 560 is disposed at a predetermined angle 4.5 degrees or parallel with respect to the center transverse axis of top surface 540. In addition, each channel 560 is spaced a predetermined distance inwardly from top surface 540. Moreover, frame 530 may have a plurality of internally threaded bores 570 for threadably receiving respective ones of externally threaded screw bolts 340 for reasons disclosed presently. In this regard, frame 530 is attached to circular seat 510 by screw bolts 340, which screw bolts 340 extend through seat 510 and which are threadably received in respective ones of bores 570, for securing frame 530 to seat 510. Frame 530 may be "LUCITE", or the like, for reducing the weight of frame 530. Extending matingly through respective ones of channels 560 and into associated slots 550 are reflector rods 320 for reflecting the sonic energy. Hence, it will be appreciated from the description hereinabove that each of the rods 320 assumes the predetermined angle of its respective channel 560 as it extends through it respective channel 560.

Figure 3:
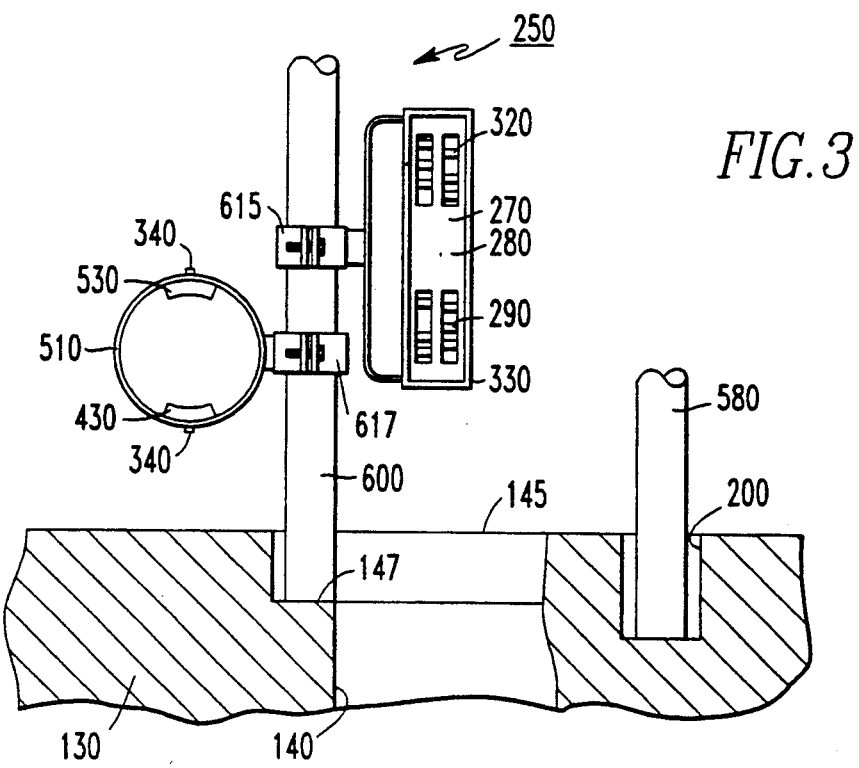
FIG. 3 shows in elevation, the calibration arrangements.
Figure 4:
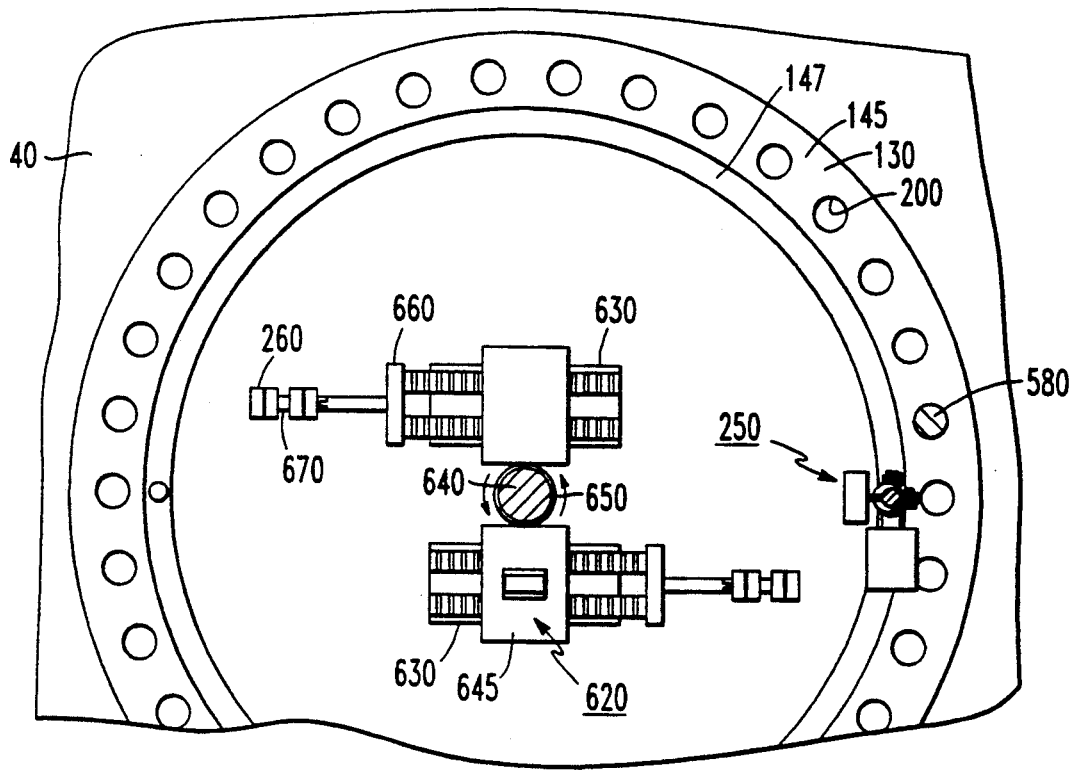
FIG. 4 is a view taken along section line 4—4 of FIG. 2.
Figure 5:
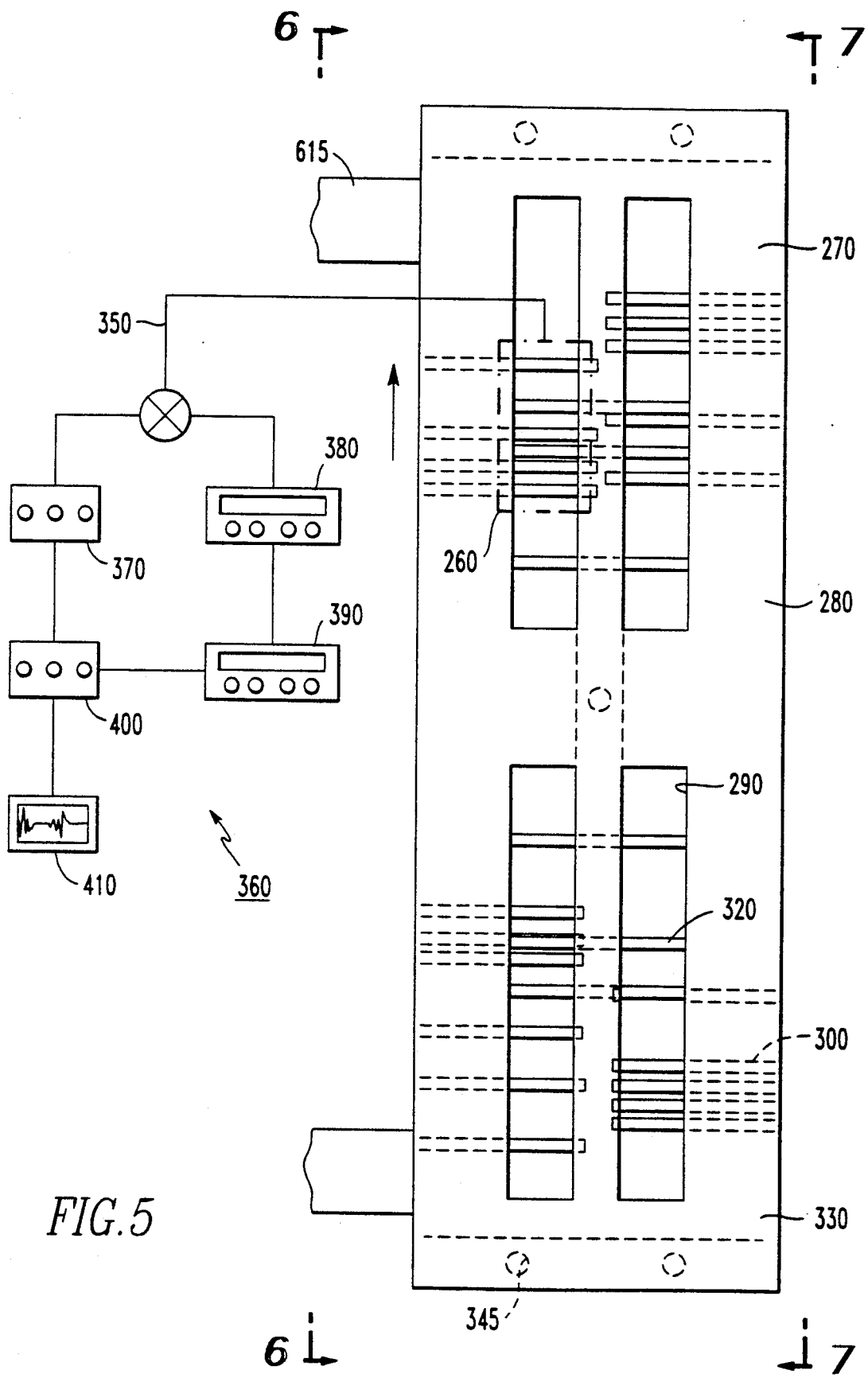
FIG. 5 shows a first embodiment calibration arrangement and the inspection instrument mounted on the calibration arrangement for calibrating the inspection instrument, the inspection instrument having the evaluation system connected thereto.

Returning now to FIGS. 2, 3 and 4, the previously mentioned manipulator assembly 120 is suspended from conveyor 100 by means of cable 110 in a manner such that manipulator assembly 120 is disposed in pressure vessel shell 130. Manipulator assembly 120 supports calibration arrangements 250/420/520 and manipulates transducer 260. In this regard, manipulator assembly 120 comprises at least one post 580 matingly received in bore 200 for supporting manipulator assembly 120 on the top end surface 145 of pressure vessel 130. Post 120 is connected to leg 600, such as by at least one bracket 590 attached to leg 600 and slidably engaging post 120. Leg 600 has an end thereof resting on ledge 147 of pressure vessel 130 for further supporting manipulator assembly 120. Frames 330, 430 and 530 are connected to leg 600, such as by removable brackets 615 and 617, as best seen in FIG. 3. Leg 600 is attached to a motor 610, also belonging to manipulator assembly 120 for reasons disclosed presently. Motor 610 is itself connected to cable 110, so that manipulator assembly 120 may be suspended therefrom. Motor 610 includes a pulley system 620 connected to an extendable manipulator arm 630 that slidably engages an elongate shaft 640, which pulley system 620 is capable of slidably moving manipulator arm 630 axially along shaft 540. Thus, manipulator arm 630 is slidably movable along the vertical longitudinal axis of shaft 640 by means of pulley system 620 as motor 610 operates pulley system 620. Manipulator arm 630 is also outwardly and inwardly extendable, by means of a motor 645 (see FIG. 4) connected thereto, in a plane generally perpendicular to the longitudinal axis of elongate shaft 640 for reasons provided hereinbelow. Slidably surrounding shaft 540 is a collar 650 which is attached to manipulator arm 630. As illustrated in FIG. 4, manipulator arm 630 is slidably rotatable about the longitudinal axis of shaft 640, such as in the direction of the curved arrows of FIG. 4. Moreover, manipulator arm 630 comprises an end effector 660. End effector 660 is capable of rotating in a 360° circle about the longitudinal axis of manipulator arm 630. End effector 660 may include a jointed member 670 to which is connected transducer 260. Jointed member 670 is capable of pivoting about an axis generally perpendicular to the axis of rotation of end effector 660. It will therefore be appreciated from the description hereinabove that manipulator assembly 120 allows transducer 260, which is connected to manipulator assembly 120, to obtain five degrees of freedom of movement for performing the inspection and for performing the calibration. That is, transducer 260 has a vertical first degree of freedom of movement as cable 110 and motor 610 vertically lowers manipulator arm 650 (and the transducer 260 connected thereto) into pressure vessel shell 130 and vertically raises manipulator arm 650 out-of-pressure vessel shell 130. Transducer 260 has a horizontal second degree of freedom of movement as extendable manipulator arm 630 outwardly and inwardly moves transducer 260. Moreover, transducer 260 has a rotatable third degree of freedom of movement as end effector 660 rotates transducer 260. Transducer 260 also has a rotatable fourth degree of freedom of movement centered about the axis of shaft 640 as motor 610 causes collar 650, and manipulator arm 650 attached thereto, to rotate about the longitudinal axis of shaft 640. In addition, transducer 260 has a fifth degree of freedom of movement as jointed member 670 pivots transducer 260. In this manner, the fore mentioned five degrees of freedom of movement allow transducer 260 to be easily and quickly disposed on inside surface 140 of vessel shell 130 and on the inner surfaces of nozzles 150/160 to perform the inspection and also easily and quickly mounted on top surfaces 280/440/540 of frames 270/430/530, respectively, to perform the recalibration.

OPERATION

Pressure vessel 10 is removed from service and closure head 170, control rod drive mechanism 210, upper internals structure 1220 and lower internals structure 230 are removed from pressure vessel 10 in the manner customarily used in the art. Next, calibration arrangements 250/420/520 and transducer 260 are connected to pressure vessel shell 130 by use of bridge 90, conveyor 100 and manipulator assembly 120. That is, bridge 90 is moved, if necessary, on rail 70 by rotating wheels 80 which rotatably slidably engage rail 70. As wheels 80 engage rail 70, motorized conveyor 100 is simultaneously caused to slide on bridge 90 until conveyor 100 is positioned above pressure vessel 10. Manipulator assembly 250, which has a previously calibrated ultrasonic transducer 260 and calibration arrangements 250/420/520 attached thereto, is vertically lowered by conveyor 100, so that post 580 engages bore 200 and so that leg 600 rests on ledge 147. Manipulator arm 250 manipulates transducer 260 to position it for ultrasonically inspecting at least surface 140 and/or nozzles 150/160 for anomalies. Before the inspection is begun, transducer 260 is calibrated to a known standard by means of a prior art steel calibration block (not shown) having a hole therein for reflecting sonic energy, the prior art calibration block being disposed externally to vessel shell 130. However, the operating response or output signals of transducer 260 may vary over time due to "drift", instrument component aging, or the like, which in turn may lead to inaccurate inspection results unless the inspection instrument is periodically re-calibrated.

Therefore, following a predetermined time period (e.g., approximately 12 hours) of inspection, transducer 260 is mounted on top surface 280 of frame 270, belonging to the first embodiment of the invention, to re-calibrate transducer 260, so that transducer 260 will accurately inspect surface 140 for anomalies. In this regard, motor 610 is operated to activate pulley system 620 so that manipulator arm 630 slides vertically along shaft 640 to position manipulator arm 630, and transducer 260 connected thereto, near frames 270/430/530 to perform the re-calibration. Motor 610 may also be operated, if necessary, to rotate manipulator arm 630 about shaft 640 in order to suitably position manipulator arm 630 near frames 270/430/530. Motor 645 may then be operated to extend manipulator arm 630 toward any of frames 270/430/530. Motors 610/645 are further operated to slidably move transducer 260, which is connected to manipulator arm 630, across top surfaces 280/440/540 that belong to frames 270/430/530, respectively.

As transducer 260 moves across slot 210 (such as in the direction illustrated by the arrow in FIG. 5), computer 400 activates pulser 330 so that pulser 330 periodically stimulates transducer 260 to cause transducer 260 to transmit a plurality of sonic energy pulses spaced apart in time. Each pulse of sonic energy travels through coupling medium 30 in slot 210 to interact with at least one of the rods 320. The rod 230 interacting with the sonic energy beam transmitted by transducer 260 reflects the sonic energy beam and produces an echo which is associated with the predetermined location of rod 230. The echo is returned through coupling medium 30 to be received by transducer 260 before another sonic pulse is transmitted by transducer 260. As transducer 260 receives the echo, it simultaneously generates a transducer output signal, which transducer output signal is indicative of the predetermined location (e.g., depth and orientation or angle from surface 280) of rod 230. Receiver 380 receives the transducer output signal and provides an analog output signal which is received by analog-to-digital converter 390. Analog-to-digital converter 390 converts the analog output signal into a digital output signal which is received by computer 400. Computer 400 evaluates the digital output signal and displays an image thereof on graphic display 410, so that the operator of evaluation system 360 may view an image of the sonic signal reflected by rod 230. Computer 400 may also print the image on a paper strip chart (not shown) for permanently recording the image displayed on display 410 for later analysis.

The second embodiment of the invention is used in substantially the same manner as the first embodiment of the invention, except that transducer 260 is moved on convex surface 440 of frame 430 in a predetermined arc (e.g., approximately 24 degrees arc). In this second embodiment of the invention, transducer 260 is mounted on top surface 440 of frame 430 to recalibrate transducer 260 so that transducer 260 will accurately inspect nozzles 150/160 for anomalies when transducer 260 moves in a semi-circular arc within nozzles 150/160. In this regard, transducer 260 is mounted on top surface 440 to span slot 470 by use of manipulator arm 250. Manipulator arm 250 is operated so as to slide transducer 260 across slot 470. In the manner previously described, transducer 260 transmits and receives sonic energy that is displayed on display 410.

The third embodiment of the invention is used in substantially the same manner as the second embodiment of the invention, except that transducer 260 is moved on top surface 540 of frame 530 along an approximately linear or transverse path (i.e., a substantially straight path having an approximate zero degree arc). In this second embodiment of the invention, transducer 260 is mounted on convex top surface 540 of frame 530 to calibrate transducer 260, so that transducer 260 will accurately inspect nozzles 150/160 for anomalies when transducer 260 moves in a straight line longitudinally along the inside surface of nozzles 150/160. In this regard, transducer 260 is mounted on top surface 540 to span a selected one of the slots 550 by use of manipulator arm 250. Manipulator arm 250 is operated so as to slide transducer 260 across slot 450. In the manner previously described, transducer 260 transmits and receives sonic energy that is displayed on display 410.

Following recalibration in the manner hereinabove described, transducer 260 is again used to inspect the pressure vessel structure, such as surface 140 and nozzles 150/160. After a predetermined interval of inspection time (e.g., an aggregate inspection time of approximately 12 hours), transducer 260 is again recalibrated in the manner previously described. After the ultrasonic inspection of pressure vessel 10 has been completed, control rod drive mechanism 210, upper internals structure 1220, and closure head 170 are returned to pressure vessel 10 and connected thereto in substantially the reverse order of their removal from pressure vessel 10. After control rod drive mechanisms 210, upper internals structure 1220, and closure head 170 are connected to pressure vessel 10, pressure vessel 10 is returned to service.

It is evident from the teachings herein that an advantage of the present invention is that it reduces maintenance costs because nonessential maintenance personnel need not leave the area of pressure vessel 10 to avoid radiation exposure during calibration of transducer 260. This is so because the calibration process is always performed entirely under water (i.e., within the reactor coolant or medium 30) which shields these nonessential maintenance personnel from radiation exposure. Another advantage of the present invention is that revenue is not lost due to delays in returning pressure vessel 10 to service because transducer 260 need not be repeatedly retrieved and reintroduced into pressure vessel 10 in order to perform the required number of recalibrations. Yet another advantage of the present invention is that radiation dose levels to essential maintenance personnel performing the actual recalibration are reduced because such personnel are not repeatedly exposed to the radioactively contaminated transducer 260 during the calibration process.

Although the invention is fully illustrated and described herein, it is not intended that the invention as illustrated and described be limited to the details shown, because various modifications may be obtained with respect to the invention without departing from the spirit of the invention or the scope of equivalents thereof. For example, rather than "LUCITE", frames 330/430/530 may be formed of a metal, such as aluminum, anodized to resist the corrosive effects of coupling medium 30. Moreover, the calibration arrangements 250/420/520 need not be exclusively used in a nuclear reactor pressure vessel; rather, calibration arrangements 250/420/520 may be used wherever it is desirable to perform remote calibration of an ultrasonic transducer intended for inspecting vessels of any type.

Therefore, what is provided are a calibration arrangement and method for calibrating an inspection instrument, such as an ultrasonic inspection instrument of the kind typically used to inspect nuclear reactor pressure vessels.

What is claimed is:

1. A calibration arrangement for calibrating an inspection instrument capable of transmitting and receiving sonic energy, the instrument capable of generating a signal in response to the sonic energy received thereby, comprising:
   (a) a frame having a surface for mounting the instrument thereon, said frame having a slot for receiving a sonic coupling medium therein and having a channel in communication with the slot, the channel having a predetermined orientation with respect to the instrument; and
   (b) a reflector extending through the channel and into the slot for reflecting the sonic energy, said reflector having the predetermined orientation of the channel as said reflector extends through the channel, whereby said reflector reflects the sonic energy as the inspection instrument transmits the sonic energy, whereby an echo associated with the predetermined orientation of said reflector is produced as said reflector reflects the sonic energy, and whereby the echo produced by said reflector travels through the coupling medium and is received by the instrument to generate the signal, the signal being indicative of the predetermined orientation of said reflector for calibrating the instrument.

2. The calibration arrangement of claim 1, wherein said reflector is formed of a solid material for reflecting a substantial amount of the sonic energy.

3. The calibration arrangement of claim 1, wherein said frame is formed of a light-weight material.

4. The calibration arrangement of claim 1, further comprising a manipulator assembly attached to the transducer for manipulating the transducer, said manipulator assembly capable of mounting the transducer on said frame.

5. A calibration arrangement for calibrating a transducer capable of transmitting and receiving sonic energy, the transducer capable of generating a plurality of transducer output signals in response to the sonic energy received thereby, comprising:
   (a) a frame having a surface for mounting the transducer thereon, said frame having a plurality of slots for receiving a sonic coupling medium therein and having a plurality of channels in communication with associated ones of the slots, each of the channels having a predetermined orientation with respect to the transducer; and
   (b) a plurality of reflectors extending through respective ones of the channels and into associated ones of the slots for reflecting the sonic energy, each of said reflectors having the predetermined orientation of its respective channel, whereby said reflectors reflect the sonic energy as said transducer transmits the sonic energy, whereby a plurality of echoes associated with the predetermined orientation of respective ones of said reflectors are produced as said reflectors reflect the sonic energy, and whereby the echoes travel through the coupling medium and is received by the transducer to generate the plurality of transducer output signals, each of the signals being indicative of the predetermined orientation of respective ones of said reflectors.

6. The calibration arrangement of claim 5, wherein said reflectors are formed of a solid material for reflecting substantially all of the sonic energy.

7. The calibration arrangement of claim 6, wherein said solid material is stainless steel.

8. The calibration arrangement of claim 5, wherein said frame is formed of a light-weight polymer material for minimizing the weight of said frame.

9. The calibration arrangement of claim 8, wherein said polymer material is "LUCITE".

10. The calibration arrangement of claim 5, further comprising an evaluation system connected to the transducer for evaluating the transducer output signals.

11. The calibration arrangement of claim 10, wherein said evaluation system comprises:

(a) a pulser device connected to the transducer for stimulating the transducer, so that the transducer transmits the sonic energy;

(b) a receiver connected to said transducer for receiving the transducer output signals as the transducer receives the echoes, said receiver providing a plurality of analog output signals as said receiver receives the transducer output signals;

(c) an analog-to-digital converter connected to said receiver for converting the analog output signals into a plurality of digital output signals;

(d) a computer connected to said analog-to-digital converter for evaluating the digital output signals and connected to said pulser device for operating said pulser device; and (e) a display connected to said computer for viewing the digital output signals evaluated by said computer.

12. The calibration arrangement of claim 5, further comprising a manipulator assembly attached to the transducer for manipulating the transducer, said manipulator assembly capable of slidably mounting the transducer on the surface of said frame and across a selected one of the slots.

13. In a nuclear reactor pressure vessel having water therein providing a sonic coupling medium, a calibration arrangement for calibrating an ultrasonic transducer capable of transmitting and receiving an ultrasound energy beam, the transducer capable of generating a plurality of transducer output signals in response to the energy beam received thereby, the calibration arrangement comprising:

(a) a frame having a surface for slidably mounting the transducer thereon, said frame having a plurality of spaced-apart slots therethrough for receiving the coupling medium therein and having a plurality of elongate spaced-apart channels therethrough in communication with associated ones of the slots, each of the channels oriented at a predetermined angle with respect to the transducer, said frame being formed of a light-weight polymer material for minimizing the weight of said frame; and (b) a plurality of elongate solid reflector rods extending matingly through respective ones of the channels and into associated ones of the slots for reflecting the energy beam as the transducer transmits the energy beam, each of said rods having the predetermined angle of its respective channel, whereby a plurality of echoes associated with the predetermined angle of respective ones of said rods are produced as the transducer slides on the surface of said frame and transmits the energy beam and as said rods reflect the echoes therefrom, and whereby each of the echoes travels through the coupling medium and is received by the transducer to generate the plurality of transducer output signals, each of the transducer output signals being indicative of the predetermined angle of respective ones of said rods.

14. The calibration arrangement of claim 13, wherein said solid rods are stainless steel.

15. The calibration arrangement of claim 12, wherein the polymer material forming said frame is "LUCITE".

16. The calibration arrangement of claim 13, wherein said frame has a generally rectangular-shaped transverse cross section for simulating a reactor pressure vessel wall.

17. The calibration arrangement of claim 13, wherein said frame has a generally arcuate-shaped transverse cross section for simulating a reactor pressure vessel nozzle.

18. The calibration arrangement of claim 13, further comprising an evaluation system electrically connected to the transducer for evaluating the transducer output signals, said evaluation system including:

(a) a pulser device electrically connected to said transducer for electrically stimulating the transducer as the transducer slides on the surface of said frame and transmits the energy beam, so that the transducer transmits the energy beam through the coupling medium and to successive ones the rods;

(b) a receiver electrically connected to the transducer for receiving the transducer output signals, said receiver providing a plurality of analog output signals as said receiver receives the transducer output signals;

(c) an analog-to-digital converter electrically connected to said receiver for converting the analog output signals into a plurality of digital output signals;

(d) a computer electrically connected to said analog-to-digital converter for evaluating the digital output signals and connected to said pulser device for operating said pulser device; and (e) a display electrically connected to said computer for viewing the digital output signals evaluated by said computer.

19. The calibration arrangement of claim 13, further comprising a manipulator assembly attached to the transducer for manipulating the transducer, said manipulator assembly capable of slidably mounting the transducer on the surface of said frame and across a selected one of the slots, said manipulator assembly including:

(a) a shaft;

(b) an elongate manipulator arm defining a longitudinal axis therethrough and slidably engaging said shaft, said manipulator arm capable of translating the transducer toward and away from said frame;

(c) an end-effector rotatably connected to said manipulator arm and connected to the transducer for rotating the transducer about the longitudinal axis of said manipulator arm; and (d) a jointed member pivotally connected to said manipulator arm and affixed to the transducer for pivoting the transducer about an axis transversely with respect to the longitudinal axis of said manipulator arm, whereby the transducer has a first degree of freedom as said manipulator arm slides on said shaft, whereby the transducer has a second degree of freedom as said manipulator arm translates, whereby the transducer has a third degree of freedom as said jointed member pivots, whereby the transducer has a fourth degree of freedom as said manipulator arm rotates about said shaft, and whereby the transducer has a fifth degree of freedom as said end-effector rotates, so that the transducer has five degrees of freedom of movement to enable the transducer to be slidably mounted on said frame by said manipulator arm.

20. A method of calibrating an inspection instrument capable of transmitting and receiving sonic energy, the instrument capable of generating a signal in response to the sonic energy received thereby, comprising the steps of:

(a) providing a frame having a surface for mounting the instrument thereon, said frame having a slot for receiving a coupling medium therein and having a channel in communication with the slot, the channel having a predetermined orientation with respect to the instrument, the channel having a reflector extending therethrough so that the reflector has the predetermined orientation of the channel and so that the reflector extends into its associated slot for reflecting the sonic energy; and (b) operating the instrument to transmit the sonic energy through the coupling medium, so that the sonic energy is intercepted by the reflector and reflected through the coupling medium to produce an echo capable of being received by the instrument, the echo being indicative of the predetermined orientation of the reflector for calibrating the instrument with respect to the predetermined orientation of the reflector.

21. The method of claim of claim 20, wherein said step of operating the instrument comprises the step of operating an evaluation system connected to the instrument for stimulating the instrument to transmit the sonic energy and for evaluating the echo received by the instrument.

22. In a nuclear reactor pressure vessel having water therein providing a sonic coupling medium, a method of calibrating an ultrasonic transducer capable of transmitting and receiving an ultrasonic energy beam, the transducer capable of generating a plurality of transducer output signals in response to the energy beam received thereby, the method comprising the steps of:

(a) disposing a frame in the coupling medium, the frame having a surface for slidably mounting the transducer thereon, the frame having a plurality of spaced-apart slots therethrough for receiving the coupling medium therein and having a plurality of elongate spaced-apart channels in communication with associated ones of the slots, each of the channels oriented at a predetermined angle with respect to the transducer, each of the channels having an elongate solid reflector rod extending matingly therethrough and into its associated slot for reflecting the sonic energy beam, each of the rods having the predetermined angle of its respective channel;

(b) operating the transducer to transmit the energy beam through the coupling medium, so that the energy beam is intercepted by the rods and reflected through the coupling medium to produce a plurality of echoes indicative of the predetermined angle of its associated rod, each of the echoes traveling through the coupling medium, so that the echoes are received by the transducer; and (c) operating an evaluation system connected to the transducer for stimulating the transducer to transmit the energy beam and for evaluating the echoes received by the transducer.

23. The method of claim 22, wherein said step of operating the evaluation system comprises the steps of:

(a) transmitting an ultrasonic energy beam by stimulating the transducer;

(b) generating transducer output signals by operating the transducer to receive the energy beam reflected by the rods;

(c) converting the analog output signals into digital output signals by operating an analog-to-digital converter connected to the transducer;

(d) evaluating the digital output signals by operating a computer connected to the digital converter; and (e) displaying the digital output signals by operating a display connected to the computer.

24. The method of claim 22, further comprising the step of operating a manipulator assembly connected to the transducer for mounting the transducer on the frame.

* * * * *